United States Patent [19]

Kälberer et al.

[11] 4,198,968

[45] Apr. 22, 1980

[54] POROUS SHAPED ARTICLE OF REGENERATED CELLULOSE ADAPTED FOR MEDICAL USE

[75] Inventors: Heinz Kälberer, Walluf; Heinrich Fauth, Mainz, both of Fed. Rep. of Germany

[73] Assignee: Hoechst Aktiengesellschaft, Frankfurt am Main, Fed. Rep. of Germany

[21] Appl. No.: 878,455

[22] Filed: Feb. 16, 1978

[30] Foreign Application Priority Data

Feb. 19, 1977 [DE] Fed. Rep. of Germany ....... 2707308

[51] Int. Cl.² ............................................. A61B 17/11
[52] U.S. Cl. .................................... 128/156; 128/296; 106/168
[58] Field of Search ............... 128/156, 284, 285, 290, 128/296; 260/17 A; 536/87–88; 428/314–315, 508, 536; 106/168, 169

[56] References Cited

U.S. PATENT DOCUMENTS

| | | | |
|---|---|---|---|
| 2,880,726 | 4/1959 | Stieg | 128/285 |
| 2,996,409 | 8/1961 | Lavely | 128/296 |
| 3,005,457 | 10/1961 | Millman et al. | 128/296 |
| 3,018,192 | 1/1962 | Hennemann et al. | 106/168 |
| 3,055,369 | 9/1962 | Graham, Jr. | 128/285 |
| 3,085,901 | 4/1963 | Lindsey et al. | 428/508 |
| 3,187,747 | 6/1965 | Burgeni et al. | 128/285 |
| 3,618,607 | 11/1971 | Ells et al. | 128/285 |
| 3,847,636 | 11/1974 | Smith | 128/296 |
| 3,961,629 | 6/1976 | Richter et al. | 128/296 |

FOREIGN PATENT DOCUMENTS

| | | |
|---|---|---|
| 959050 | 2/1957 | Fed. Rep. of Germany. |
| 1079796 | 4/1960 | Fed. Rep. of Germany. |
| 2357079 | 5/1975 | Fed. Rep. of Germany. |
| 2364628 | 6/1975 | Fed. Rep. of Germany. |
| 1108066 | 4/1968 | United Kingdom. |
| 1228849 | 4/1971 | United Kingdom. |
| 1470726 | 4/1977 | United Kingdom. |
| 1492040 | 11/1977 | United Kingdom. |

*Primary Examiner*—Robert W. Michell
*Assistant Examiner*—C. F. Rosenbaum
*Attorney, Agent, or Firm*—Schwartz, Jeffery, Schwaab, Mack, Blumenthal & Koch

[57] ABSTRACT

A porous shaped article adapted for medicinal use is disclosed which comprises a porous regenerated cellulose the entire surface of which is covered with a coating comprising a hydrophilizingly effective amount of at least one wetting agent and a substantially water insoluble chemically modified cellulose ether which is crosslinked carboxymethylcellulose or a reaction product of a partially etherified cellulose and a chemical modifying agent which is capable of reacting with the free hydroxy groups of the etherified cellulose.

The articles are coated by first impregnating same with a cellulose ether solution and then treating the impregnated article with a solution of the modifying agent. The wetting agent may be added to either of these steps.

The coated articles retain a high absorption capacity for liquids, yet do not release any substantial amounts of turbidifying impurities into a surrounding liquid and therefore are especially suited for medical uses.

12 Claims, 2 Drawing Figures

POROUS SHAPED ARTICLE OF REGENERATED CELLULOSE ADAPTED FOR MEDICAL USE

BACKGROUND OF THE INVENTION

This invention relates to a porous shaped article, in particular, sponge-like article, e.g., sponge cloth, of regenerated cellulose which is sufficiently void of impurities to be adapted for medical purposes and also to a process for the manufacture of this shaped article.

Processes for preparing porous shaped articles of cellulose hydrate are known in the art. For this purpose, cellulose is first converted into viscose. In order to cause the formation of pores, a pore forming agent, such as salt grains, e.g. crystals of Glauber's salt of appropriate grain size, are usually incorporated into the viscose, and, if desired, reinforcing fibers, e.g. cotton fibers of 12 to 15 mm length, may be incorporated as well. Then the mass is coagulated in a coagulating bath under the influence of heat, e.g. is coagulated in a water bath at approximately 100° C. In case of preparing a flat shaped porous article, a layer of the mass advantageously is applied to an endless belt, by means of which it is introduced into the coagulating bath. In the water bath, a major portion of pore forming agent is eliminated, e.g. the salt is dissolved and washed away. The porous shaped article then passes through a precipitating bath containing aqueous sulfuric acid and, if appropriate, a chlorite bleaching bath. Next follows a washing step where the porous shaped article is thoroughly washed with water. Then it is dried. After drying, it may be cut to the desired size. Porous shaped articles of regenerated cellulose which are to be used for medical purposes must comply with strict requirements for chemical purity, comparable to the purity standards which are applied to medicinal bandaging material and gauze bandages of cellulose. There have been hardly any difficulties to comply with these requirements as far as the content of dyes, optical brighteners, acids, heavy metal ions, alkali, chlorine ions, sulfate ions, sulfide ions and calcium ions is concerned. However, regarding the degree of turbidity of an aqueous extract from the porous shaped article, such standards cannot be met by the conventional porous shaped articles of regenerated cellulose. The degree of turbidity of the aqueous extract is a measure of the amount of non-fixed cellulose particles which can be washed out of the article. In the case of gauze bandages, the degree of turbidity of the aqueous extract is determined as follows: 10 g of a gauze bandage are placed in a beaker, are covered with 100 ml of boiling hot distilled water and are then heated for fifteen minutes in the boiling water bath. 5 ml of the aqueous extract which is obtained by squeezing or sucking off from the bandage must not be more turbid than the following comparative solution: To 5 ml of a mixture of 2 ml of 0.01 N hydrochloric acid and 98 ml of distilled water, 0.5 ml of 0.1 N silver nitrate solution is added. The comparison is made five minutes after the addition of the silver nitrate solution against a dark background and with impinging light. When the permeability to light of this comparison solution is determined with the aid of a beaker colorimeter (manufacturer: Lange, Berlin) using water as a blank, a permeability value of 85 to 86 percent is obtained, i.e. the aqueous extract of a porous shaped article suitable for medical purposes must have a permeability to light of 85 to 100 percent as compared to clear water; yet, the permeability value of the hereto known porous shaped articles of regenerated cellulose is below 65 percent.

Up to the present, porous shaped articles which have been used in the medical field have been applied only externally as pads, for example, in dental medicine or ophthalmology. It is, however, impossible to use them for surgical purposes, in particular as tampons, since there is a danger that cellulose particles are washed out of the product and are left in the wound and cause inflammations.

SUMMARY OF THE INVENTION

It is an object of the present invention to provide a porous shaped article, in particular a sponge-like article or a sponge cloth, of regenerated cellulose, which is sufficiently void of chemical impurities to be adapted for medicinal use, in particular for use in the field of surgery.

It is a special object of the present invention to provide such an article which is substantially free of unfixed cellulose particles which can be washed out during the use of the article.

It is a further object of the present invention to provide such a porous shaped article, wherein the absorption capacity towards water and aqueous solutions and the mechanical strength of the conventional porous regenerated cellulose material is retained.

In order to accomplish the foregoing objects, according to the present invention, there is provided a porous shaped article adapted for medicinal use, comprising a porous regenerated cellulose, the entire surface of which is covered with a coating comprising a hydrophilizingly effective amount of at least one wetting agent and a substantially water insoluble chemically modified cellulose ether which is crosslinked carboxymethylcellulose or a reaction product of a partially etherified cellulose and a chemical modifying agent which is capable of reacting with the free hydroxy groups of the etherified cellulose in an alkaline reaction medium.

The chemical modifying agent suitably is selected from the group consisting of a compound which contains at least one group which is functional towards cellulose. Such agents have, for example, at least two groups of the formulae

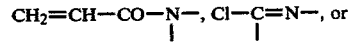

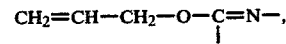

or are epoxy derivatives containing at least one further functional group, α,α-dichloro carboxylic acids, polychlorinated alcohols and polychlorinated 5- or 6-membered N-containing heterocyclic compounds. Vinylsulfonamide and acrylamides of the formula

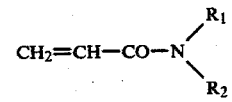

wherein $R_1$ is hydroxyl, an acylamino group, or an esterified carbamino group, and $R_2$ is hydrogen or the carboxyl group, are agents with one group which is functional towards cellulose.

Substantially water soluble alkali salts of carboxy methyl cellulose is preferably used as the cellulose ether, which if desired, can be crosslinked by means of a crosslinking agent without addition of one of the above-mentioned chemical modifying agents.

Due to their absorption capacity for liquids and their physiological compatability toward body liquids, the porous shaped articles according to the present invention, in particular sponge cloths and tampons, are useful in the medical art and can be applied to injured portions of the body for absorbing liquids which originate from the injured portions of the body.

According to the present invention, there is further provided a process for preparing the above-defined porous shaped article which comprises the steps of:

a. contacting a porous shaped article of regenerated cellulose with a first aqueous liquid containing from about 0.01 to about 5% by weight of at least one substantially water soluble cellulose ether to apply a liquid coating of said first liquid to the entire surface of the porous shaped article;

b. removing any amount of said first liquid which is in excess of said liquid coating from the treated porous shaped article;

c. treating the liquid coated porous shaped article with a second aqueous liquid containing at least 10% by weight, preferably at least 50% by weight, relative to the amount of cellulose ether used, of at least one chemical agent which is capable of transforming the largely water soluble cellulose ether into a substantially water insoluble chemically modified cellulose ether and which is selected from the group consisting of a chemical modifying agent which is capable of reacting with free hydroxy groups in the cellulose ether in an alkaline reaction medium to form a substantially water insoluble reaction product and an agent for crosslinking carboxy methyl cellulose comprising a salt of a divalent or a trivalent metal ion;

d. applying to the entire surface of the porous shaped article an hydrophilizing amount of at least one wetting agent, if required, neutralizing and washing the article to free it from salt; and e. drying the treated porous shaped article.

The wetting agent can either be applied together with the cellulose ether in the first aqueous liquid or together with chemical agent in the second aqueous liquid.

Further objects, features and advantages of the present invention will become apparent from the detailed description of the invention and its preferred embodiments which follows when considered together with the accompanying figures of drawing.

DETAILED DESCRIPTION OF THE PREFERRED EMBODIMENTS

Figure 1:
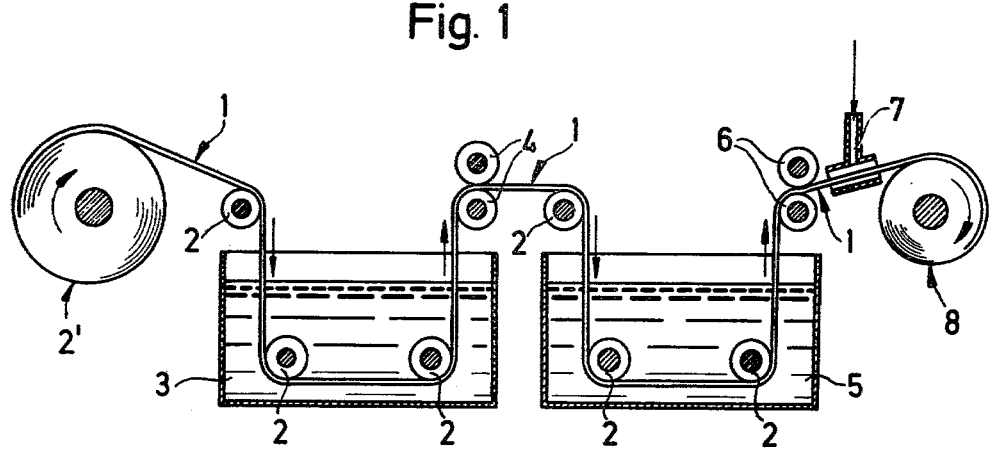
FIG. 1 is a schematic view of an assembly for preparing the shaped article according to an embodiment of the process according to the present invention.

Surprisingly, it has now been found that the aqueous extract of a porous shaped article of regenerated cellulose has an improved degree of turbidity, if the shaped article comprises a coating comprising a substantially water insoluble chemically modified cellulose ether and a hydrophilizingly effective amount of a wetting agent on its entire surface.

The term "porous shaped article" as it is applied in the present specification and claims is meant to denote articles of various shapes having a porous structure, e.g., sponge-like materials. Preferred are flat sheet-like materials which have a spongy structure, such as sponge cloth, or otherwise shaped sponges, e.g. tampons, etc. The term "entire exterior surface" as it is used in the present specification and claims, is meant to denote the outside surface of the article and the surface of those pores which start from the visible outside surface.

The porous shaped article according to the present invention is prepared by applying the above-defined coating to a conventional porous shaped article of regenerated cellulose which is produced by coagulation of viscose in a known manner, e.g. according to the above-described process. However, in view of the intended medical application of the final product, care has to be taken that the resulting porous shaped article does not contain toxic compounds or impurities. The final thorough washing with water must, therefore, be carried out very carefully, optionally using salt-free water. It is also not permissible to add dyes or optical brighteners.

The porous article is shaped by known methods, for example by compressing and/or cutting, e.g. cutting a web of sponge cloth material.

The substantial amounts of the chemically modified cellulose ether and the hydrophilizing wetting agent are present on the entire surface of the porous shaped article, yet it is also possible that these compounds penetrate into the interior of the shaped article up to a depth of a few millimeters. In the present invention it is, however, essential that the coating comprising the chemically modified cellulose ether and the wetting agent covers the entire surface of the porous shaped article.

The term "cellulose ether" as it is applied in the present specification and claims is meant to denote cellulose derivatives wherein part of the hydroxy groups in the cellulose molecule are etherified. It is preferred that the degree of substitution is sufficiently high, to ensure a large extent of water solubility of the unmodified cellulose ether. Suitable are: carboxy methyl cellulose, i.e. alkali salts of carboxy methyl cellulose, alkylethers of cellulose, e.g., methyl or ethyl cellulose, hydroxy alkylethers of cellulose, e.g., hydroxy ethyl or hydroxy propyl cellulose, alkyl hydroxy alkylethers of cellulose, e.g., methyl or ethyl hydroxy ethyl cellulose or methyl or ethyl hydroxy propyl cellulose, alkyl carboxy methyl ethers of cellulose, hydroxy alkyl carboxy methyl ethers of cellulose and alkyl hydroxy alkyl carboxy methyl ethers of cellulose. The alkyl groups within these cellulose ethers preferably are lower alkyl groups, preferably containing 1 to 3 carbon atoms.

These cellulose ethers are further chemically modified by reaction in an alkaline medium with at least 10% by weight, preferably at least 50% by weight, relative to the amount of cellulose ether used, of a chemical modifying agent, which is capable of reacting with the free hydroxy groups in the cellulose ether molecules, in particular a crosslinking agent, in order to form a substantially water insoluble chemically modified cellulose ether.

Suitable crosslinking agents for cellulose ethers are well known in the art. They are chemical compounds which are polyfunctional towards cellulose, e.g., compounds comprising at least two groups functional towards cellulose which are the acrylamido group

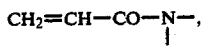

the chloroazomethine group

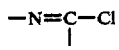

or the allyloxy azomethine group

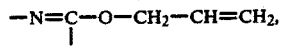

polyfunctional epoxy compounds, e.g., epihalohydrins, in particular epichlorohydrin, or bis-epoxy lower alkyl ethers, polychlorinated alcohols and/or 5- or 6-membered N-containing heterocyclic compounds, or dichloro carboxylic acids. Examples of such suitable crosslinking agents are: bis-acrylamido acetic acid; dimethylolmethylene-bis-acrylamide; methylene-bis-acrylamide; tri- and tetrachloropyrimidine; cyanuric chloride; epichlorohydrin, dichloro acetic acid; diepoxides or their precursors, di-α-halohydrins.

Crosslinked cellulose ethers of these types and their preparation are described in the U.S. Pat. Nos. 3,589,364 and 3,936,441 and the U.S. patent application Ser. No. 682,326 now U.S. Pat. No. 4,068,068 corresponding to the German Offenlegungsschrift No. 25 19 927, the disclosure of all of which is hereby incorporated by reference.

Suitable non-crosslinking modifying agents are: vinylsulfonamide or acrylamides of the formula

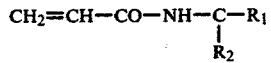

wherein $R_1$ is hydroxyl or an acylamino or an esterified carbamino group, such as formylamino or acetylamino. If $R_1$ is an esterified carbamino group, it is suitably esterified with an aliphatic alcohol containing up to 5 carbon atoms. This alcohol may be substituted by lower alkoxy, in particular methoxy. $R_2$ is hydrogen or carboxyl. Examples of such suitable modifying agents are: N-methylol acrylamide; N-(acrylamido methylene)-acetamide; N-(acrylamido methylene)-formamide; N-(acrylamido methylene)-amyl urethane; N-(acrylamido methylene)-methyl urethane; N-(acrylamido carboxy methylene)-ethyl urethane; N-(acrylamido methylene)-methoxy ethyl urethane; vinyl sulfonamide. Modified cellulose ethers of these types and their preparation are described in U.S. Pat. No. 3,965,091, the disclosure of which is hereby incorporated by reference.

A particularly advantageous crosslinked cellulose ether is a carboxy methyl cellulose, the alkali salt of which is crosslinked by means of di- or trivalent metal ions and wherein the average degree of etherification (DS) is such that, without crosslinking, the alkali salt would be soluble in water. Aluminium ions are especially suitable for crosslinking such a salt of carboxy methyl cellulose.

The added amount of the chemically modified, in particular crosslinked, cellulose ether may be varied within wide limits, but in order to obtain a satisfactory improvement of the degree of turbidity of the aqueous extract of the final porous shaped article, a minimum amount of about 0.3 percent by weight is required, relative to the weight of the porous shaped article. On the other hand, increasing this amount up to more than about 10 percent would adversely affect the absorption effectiveness of the article, e.g. would result in too slow of an absorption speed for liquids. The amount of cellulose ether which is applied influences not at all or only slightly the mechanical strength of the porous shaped article.

Another parameter which may also be varied within wide limits is the degree of modification or crosslinking of the cellulose ether. If small amounts of a crosslinking agent are used, for example, in the case of carboxymethyl cellulose, 3 to 10 percent by weight of epichlorohydrin relative to the sodium carboxy methyl cellulose, highly swellable products are obtained. Using a higher degree of crosslinking, the swellability of the cellulose ether is greatly reduced and, at the same time, its water-insoluble fraction is increased.

The hydrophilizing wetting agent serves to improve the speed at which aqueous liquids are absorbed by the porous shaped article and which is reduced by the presence of the modified, preferably crosslinked cellulose ether. For this purpose, conventional hydrophilizing substances, preferably anionic surfactants, are used, which increase the wettability of the surface of a body toward aqueous liquids. These substances comprise, in particular, the known wetting agents comprising fatty alcohol sulfates, e.g. alkali salts of monoalkyl sulfates containing about 8 to 18 carbon atoms, such as sodium, lauryl sulfate, alkylaryl sulfonates, e.g. alkali salts of alkyl benzene sulfonates, wherein the alkyl contains about 8 to 18 carbon atoms, such as sodium dodecylbenzene sulfonate, and dialkyl sulfimides, e.g. alkali salts of dialkyl sulfimides containing an alkyl of from about 8 to 18 carbon atoms. Depending on the amount of cellulose ether applied, the porous shaped article preferably contains 0.3 to 1.5 percent by weight of a wetting agent.

It is a further object of the present invention to provide a process for preparing the above-defined porous shaped article which is adapted for medical purposes. In this process the surface of a conventional porous shaped article of regenerated cellulose which is prepared in the usual manner by coagulation of viscose and which is free from toxic compounds and impurities is brought into contact with an aqueous solution of 0.01 to 5 percent by weight of at least one cellulose ether which is soluble in water to at least a major extent; any excess solution is then removed and an aqueous liquid containing at least 10% by weight, preferably at least 50% by weight, relative to the amount of cellulose ether used, of at least one modifying and/or crosslinking agent for the cellulose ether is allowed to act upon the material; whereby one or several hydrophilizing wetting agents are added in one or several of these process steps. Subsequently, the porous shaped article is, if required, neutralized and washed free from salt and is freed from solvent, preferably by drying in air at a moderate temperature. It is then compressed and cut to the desired size. All of the process steps are preferably carried out at room temperature or at a slightly raised temperature. If slowly reacting modifying or crosslinking agents are used, the temperature must be appropriately increased, if necessary to more than 50° C.

The wetting agent is preferably applied to the surface of the porous shaped article in an aqueous solution containing from about 0.05 to about 3% by weight of the agent together with the cellulose ether and/or with the modifying or crosslinking agent.

Figure 2:
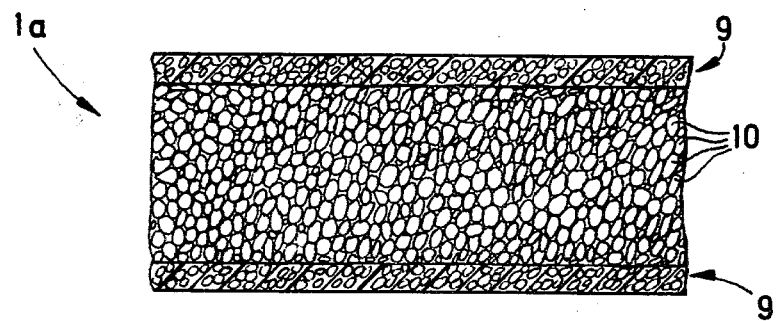
FIG. 2 is a schematic view of a cross section of a flat shaped porous article according to the invention.

The following example and FIGS. 1 and 2 serve to further illustrate the invention without constituting any limitation thereof.

Referring to FIG. 1 of the drawing, a web of sponge cloth 1 which has been produced in a known manner by coagulation of viscose is wound off from a supply roll 2' and is guided over the rolls 2. It first passes a water bath 3 containing an aqueous solution of 0.5% by weight of sodium carboxy methyl cellulose (Na-CMC) having a temperature of about 15° C. The web of sponge cloth remains in the water bath for about 6 to 7 seconds. In the form of a 2% aqueous solution, the Na-CMC exhibits a viscosity of about 30 cp (20° C.), as determined in a Höppler falling-ball viscosimeter. Subsequently, the absorbed solution is removed from the web of sponge cloth with the aid of the squeeze rolls 4. In another bath 5, containing a weakly acid aqueous solution of 0.5 percent by weight of aluminium sulfate and 0.1 percent by weight of a wetting agent containing a dialkyl sulfimide salt, e.g., the commercial product Leophen® (manufacturer: BASF, Ludwigshafen), the carboxy methyl cellulose is crosslinked. The web of sponge cloth is then squeezed again by means of the rolls 6 and the remaining solvent is removed by a fan 7, taking care that the web is not heated to a temperature of above about 100° C.

The process may be modified, e.g., by adding to the bath 5 as a modifying agent, in addition to the wetting agent, an alkaline aqueous solution (pH value preferably 8 to 9) comprising about 30 to 50 percent by weight of dimethylol methylene-bis-acrylamide or 70 to 80 percent by weight of methylene-bis-acrylamide or 50 to 70 percent by weight of N-methylol acrylamide at temperatures of above 50° C. Following squeezing the web of sponge cloth by means of rolls, the web is passed through further baths (not shown), where is is neutralized, e.g., by using dilute hydrochloric acid or sulphuric acid, freed from salt by washing in salt-free water, squeezed again and dried.

Finally, the web of sponge cloth is wound up onto a roll 8, as shown in FIG. 1, or it is compressed to one fifth of its original thickness and cut to the desired size.

For measuring the degree of turbidity of the aqueous extract of the porous shaped article, the following method is used which is similar to the standard method for testing gauze bandages, but which includes slight modifications which are necessitated by the strong absorption capacity of the material:

10 g of the sponge cloth to be tested are placed in a beaker, are covered with 500 ml of distilled water and are then vigorously kneaded for about 2 minutes. After the thoroughly squeezed cloth has been removed therefrom, the aqueous extract is concentrated to 100 ml.

The degree of turbidity is measured in a beaker colorimeter (manufacturer: Lange, Berlin), the indicating instrument of which is adjusted to 100 percent permeability, using water as a blank. The aqueous extract of the sponge cloth under examination, concentrated to 100 ml, must not be more turbid than the following comparison solution:

5 ml of a mixture of 2 ml of 0.01 n hydrochloric acid and 98 ml of water are mixed with 0.5 ml of a 0.1 n silver nitrate solution. The comparison is made 5 minutes after the addition of the silver nitrate solution. The solution exhibits an easily reproducible turbidity value showing a permeability of 85 to 86 percent. In order to comply with the purity requirements for medical application, the permeability values of the aqueous extract must, therefore, be between 85 and 100 percent. The permeability of untreated sponge cloths is about 55 to 65 percent, whereas in the foregoing examples, the permeability values of the final product are between about 91 and 93 percent. In order to determine the absorption speed of the treated sponge cloth, small triangular pieces are cut from the sample by means of scissors. The pieces exhibit a height of 17 mm, a width at the base of 8 mm, with an allowance of ±1.5 mm, and a thickness of between 1.2 and 1.8 mm. Measurements are carried out using a 0.9 percent sodium chloride solution, and for timing a stop watch is used. By means of a graduated pipet, 0.5 ml of the NaCl solution is transferred into the rim of a Petri dish, inclined 45°, to form a coherent drop.

The triangular piece of sponge cloth is taken up with tweezers, its tip is dipped into the middle of the drop and the time during which the drop is completely absorbed is measured. This time is determined in less than 3 seconds. The porous shaped article 1a, which is shown in cross section in FIG. 2 as an example of an embodiment of the invention, is a part of a sponge cloth, the entire surface 9 of which is treated according to the invention and which has pores 10. These details and the thickness of the sponge cloth are not drawn true to scale.

What is claimed is:

1. A porous shaped article adapted for medicinal use, comprising a regenerated cellulose having a cellular structure the entire exterior surface of which is covered with a coating comprising a hydrophilizingly effective amount of at least one wetting agent and a substantially water insoluble chemically modified cellulose ether which is crosslinked carboxyl methyl cellulose or a reaction product of a partially etherified cellulose and a chemical modifying agent, which reaction product is obtained by reacting the chemical modifying agent with free hydroxy groups of the etherified cellulose in an alkaline reaction medium.

2. The shaped article as defined in claim 1, wherein the chemical modifying agent is selected from the group consisting of a compound which contains at least one group which is functional toward cellulose selected from groups of the formulae

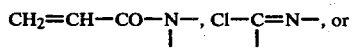

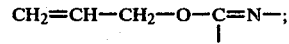

epoxy derivatives containing at least one further functional group; α,α-dichloro carboxylic acids; polychlorinated alcohols; polychlorinated 5- or 6-membered N-containing heterocyclic compounds; vinylsulfonamide; and acrylamides of the formula

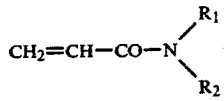

wherein $R_1$ is hydroxyl, an acylamino group or an esterified carbamino group and $R_2$ is hydrogen or carboxyl.

3. The shaped article as defined in claim 1, wherein the partially etherified cellulose is a carboxymethyl cellulose.

4. The shaped article as defined in claim 1, wherein the chemically modified cellulose ether is a crosslinked carboxy methyl cellulose.

5. The shaped article as defined in claim 4, wherein the crosslinked carboxy methyl cellulose is the crosslinked product which is obtained by treating a substantially water soluble alkali salt of carboxy methyl cellulose with a crosslinking agent comprising a salt of a divalent metal ion or a trivalent metal ion.

6. The shaped article as defined in claim 5, wherein the crosslinking agent comprises an aluminum salt.

7. The shaped article as defined in claim 1, which comprises a flat shaped article.

8. The shaped article as defined in claim 7, which comprises a sponge cloth.

9. The shaped article as defined in claim 1, which comprises an amount of about 0.3 to about 10% by weight of the chemically modified cellulose ether relative to the weight of the porous shaped article.

10. The shaped article as defined in claim 1, wherein the amount of the wetting agent is from about 0.3 to about 1.5% by weight of the porous shaped article.

11. A method for absorbing body fluids which originate at an injured portion of the body, comprising the step of applying a shaped article as defined in claim 1 to the injured portion of the body.

12. The method as defined in claim 11, wherein said shaped article is applied to an internal portion of the body.

* * * * *